(12) United States Patent
Kawasaki

(10) Patent No.: US 9,840,535 B2
(45) Date of Patent: Dec. 12, 2017

(54) METHOD OF RECOVERING PEPTIDE AND METHOD OF DETECTING PEPTIDE

(71) Applicant: SYSMEX CORPORATION, Kobe-shi, Hyogo (JP)

(72) Inventor: Kana Kawasaki, Kobe (JP)

(73) Assignee: SYSMEX CORPORATION, Kobe-shi, Hyogo (JP)

( * ) Notice: Subject to any disclaimer, the term of this patent is extended or adjusted under 35 U.S.C. 154(b) by 0 days.

(21) Appl. No.: 14/596,334

(22) Filed: Jan. 14, 2015

(65) Prior Publication Data
US 2015/0203533 A1 Jul. 23, 2015

(30) Foreign Application Priority Data

Jan. 23, 2014 (JP) .................................. 2014-010597

(51) Int. Cl.
*C07K 1/30* (2006.01)
*G01N 33/68* (2006.01)
*C07K 1/14* (2006.01)
*G01N 21/64* (2006.01)

(52) U.S. Cl.
CPC ................ *C07K 1/30* (2013.01); *C07K 1/145* (2013.01); *G01N 33/6803* (2013.01); *G01N 2021/6417* (2013.01)

(58) Field of Classification Search
None
See application file for complete search history.

(56) References Cited

U.S. PATENT DOCUMENTS

2012/0277407 A1* 11/2012 Yamamoto ............... C07K 1/34
530/344

OTHER PUBLICATIONS

Whitney et al., Individuality and variation in gene expression patterns in human blood, PNAS vol. 100 No. 4, Feb. 18, 2003.*
Mark S. Lowenthal, et al., "Analysis of Albumin-Associated Peptides and Proteins from Ovarian Cancer Patients", Oak Ridge Conference, Clinical Chemistry 51, No. 10, 2005, pp. 1933-1945.

* cited by examiner

*Primary Examiner* — Suzanne M Noakes
*Assistant Examiner* — Stephen Chong
(74) *Attorney, Agent, or Firm* — Sughrue Mion, PLLC

(57) ABSTRACT

Disclosed is a method of recovering a peptide, including: mixing a liquid sample containing a complex of peptide and protein in blood with a reagent containing a neutral amino acid, an acidic amino acid or both the neutral and acidic amino acids to liberate the peptide from the protein in blood; and recovering the liberated peptide.

6 Claims, 1 Drawing Sheet

METHOD OF RECOVERING PEPTIDE AND METHOD OF DETECTING PEPTIDE

TECHNICAL FIELD

The present invention relates to a method of recovering a peptide from a liquid sample such as blood, and a method of detecting a peptide from a liquid sample such as blood.

BACKGROUND

There is a wide variety of peptides in blood. These peptides include peptides that indicate the differences in concentrations in blood between a living body with healthy and specific pathologic condition. Such peptides are useful as biomarkers for diseases in clinical test fields.

A protein such as albumin or globulin is contained in the blood (hereinafter also referred to as "protein in blood"). Peptides bind to the protein in blood in many cases. Therefore, in detection of peptides, it is preferable to liberate the peptides from the protein in blood. As a technique of liberating a peptide, there is a technique in US Patent Application Publication No. 2012/0277407, which is herein incorporated by reference. The method described in US Patent Application Publication No. 2012/0277407 is a method comprising heat-treating a solution containing a complex of peptide and albumin to form a non-peptide binding self-aggregate of albumin and liberating the peptide from the albumin.

SUMMARY OF THE INVENTION

The scope of the present invention is defined solely by the appended claims, and is not affected to any degree by the statements within this summary.

As a result of intensive studies, the present inventor has found that peptides can be recovered or detected at a high recovery rate or high purification degree by mixing a liquid sample containing a complex of peptide and protein in blood with a reagent containing a specific amino acid and completed the present invention.

Thus, the present invention provides a method of recovering a peptide comprising: liberating a peptide from a protein in blood by mixing a liquid sample containing a complex of the peptide and the protein in blood with a reagent containing a neutral amino acid, an acidic amino acid or both; and recovering the liberated peptide.

The present invention also provides a method of a method of detecting a peptide comprising: liberating a peptide from a protein in blood by mixing a liquid sample containing a complex of the peptide and the protein in blood with a reagent containing a neutral amino acid, an acidic amino acid or both; and detecting the liberated peptide.

The present invention also provides a method of detecting a peptide, comprising: liberating a peptide from a protein in blood and forming a precipitate of the protein in blood by (i) mixing a liquid sample containing a complex of the peptide and the protein in blood with a reagent containing a neutral amino acid, an acidic amino acid or both, and (ii) heating the mixture of the liquid sample and the reagent to the range of 120° C. or higher and 260° C. or lower; recovering the liberated peptide; and detecting the recovered peptide.

DETAILED DESCRIPTION OF THE PREFERRED EMBODIMENTS

Figure 1A:
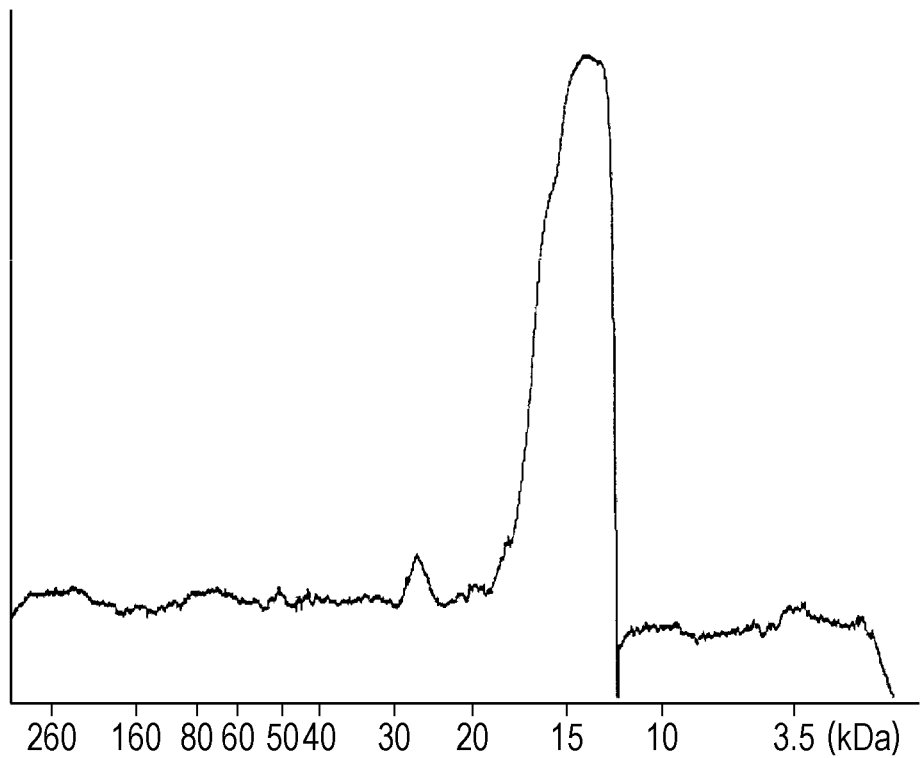
FIG. 1A is a graph showing the band intensity of SDS-PAGE gel.

The liberating step of the method of recovering a peptide of the present disclosure (hereinafter also simply referred to as "recovery method") is a step of liberating the peptide from the protein in blood by mixing a liquid sample containing a complex of peptide and protein in blood with a reagent containing a neutral amino acid, an acidic amino acid or both the neutral and acidic amino acids (hereinafter also referred to as "amino acid containing reagent").

In a preferred embodiment, the liquid sample is a biological sample. Examples of the biological sample include body fluid such as blood collected from a living body. Examples thereof also include plasma and serum obtained from blood. The liquid sample may be diluted for use. Those skilled in the art are able to set the dilution rate, as appropriate.

The "protein in blood" used herein means a protein present in the blood, such as albumin or globulin. The protein in blood binds to the peptide described below in blood to form a complex. The peptide is liberated through the liberating step of the embodiment of the present invention. The protein in blood after liberation of the peptide is aggregated and precipitated during the treatment in the liberating step.

In the embodiment, the peptide to be recovered is not particularly limited, and it may be a naturally occurring peptide or a synthetic peptide. The length of the peptide is not particularly limited as long as the peptide is recovered by the method of the present disclosure. A relatively large size of polypeptide (for example, the protein in blood) among polypeptides in the liquid sample is aggregated and precipitated by the treatment in the liberating step, meanwhile, a relatively small size of polypeptide (for example, oligopeptide) is liberated in the solution. The liberated polypeptide is a "peptide" that can be recovered by the method of the present disclosure. Not all the polypeptides in the liquid sample are precipitated or liberated completely. Depending on the polypeptides, some of the polypeptides are contained in precipitated aggregates and also are contained in a liberated component. Such polypeptides are contained in the liberated component (for example, supernatant) and they can be recovered. Thus, these polypeptides are included in the "peptide". According to the method of the present disclosure, when an amino acid is a peptide having about 130 residues, the amino acid is liberated in a sample. Accordingly, a peptide having less than 130 residues is suitable for recovery. However, the present invention is not limited thereto. When not only polypeptides originally present in a liquid sample but also polypeptides fragmented in the process of being treated by the method of the present disclosure are contained in the liberated component, these polypeptides are included in the "peptide".

In the embodiment, the isoelectric point of the peptide is not particularly limited. The peptide may be any of a basic peptide, an acidic peptide, and a neutral peptide.

In the embodiment, the peptide may be derived from molecules produced in a living body or may be derived from molecules introduced from outside a living body. Examples of the peptide derived from molecules produced in a living body include peptides produced in a living body and fragments of polypeptides produced in a living body.

In the embodiment, the peptide may be a biomarker present in the blood. Examples of the peptide as the biomarker include ghrelin, brain natriuretic peptide (BNP), adrenocorticotropichormone (ACTH), atrial natriuretic peptide (ANP), bradykinin, α-endorphin, C-peptide, C3f fragment, ITIH4 fragment, and Aβpeptide. However, they are not limited thereto. That is, the peptide to be liberated can be one that has an unidentified novel sequence of amino acids.

When a biomarker is detected, the method of the embodiment of the present invention can be used to obtain, for example, information about the presence of a specific disease and the stage of progression of the disease. That is, it is assumed that information providing an indication of determining the presence of a disease or the stage of progression of the disease is obtained by recovering a peptide, biomarker from a biological sample by the method of the embodiment of the present invention, and detecting the recovered peptide qualitatively and/or quantitatively.

In the embodiment, the peptide may be a polypeptide administered into a living body, a metabolite thereof or a fragment of these polypeptides. In this case, the method of the embodiment of the present invention may be used to obtain information about drug susceptibility. That is, it is assumed that information providing an indication of determining the sensitivity of a drug is obtained by recovering a polypeptide, drug administered to a living body or a metabolite thereof by the method of the embodiment of the present invention and detecting the recovered peptide qualitatively and/or quantitatively.

In the embodiment, the peptide may be not a peptide derived from a living body being examined, but a peptide introduced into a living body from outside a living body. Examples thereof include peptides derived from pathogens (bacteria, viruses, etc.). In this case, the method of the embodiment of the present invention may be used to obtain information, for example, about infection by pathogens. That is, it is assumed that information providing an indication of determining the infection by pathogens is obtained by recovering a peptide derived from proteins including pathogens or a peptide derived from toxins produced by pathogens (for example, verotoxin) from a biological sample by the method of the embodiment of the present invention, and detecting the recovered peptide qualitatively and/or quantitatively.

A basic amino acid is not used in the embodiment. Since the basic amino acid is used as a protein aggregation inhibitor, it is considered not to be suitable for a method comprising: aggregating proteins in blood; and recovering peptides, like the embodiment of the present invention. Therefore, in the embodiment of the present invention, a neutral amino acid or an acidic amino acid is used. Examples of the neutral amino acid include glycine, threonine, asparagine, serine, methionine, valine, tryptophan, glutamine, isoleucine, phenylalanine, alanine, proline, leucine, and cysteine. Examples of the acidic amino acid include aspartic acid and glutamic acid. Two or more neutral amino acids may be used, and two or more acidic amino acids may be used. One or more neutral amino acids may be used in combination with one or more acidic amino acids. The amino acids may be L- or D-isomer forms and may be synthetic or naturally occurring.

In the embodiment, "the amino acid containing reagent" is not particularly limited as long as it contains at least one of the above amino acids. The reagent may be in the form of a solid or liquid. Preferably, the reagent is a solid.

In a case where the amino acid containing reagent is a solid, the reagent may be any of the amino acids themselves listed above or may be an amino acid mixture containing at least one of the amino acids listed above or may further contain components other than the amino acids listed above within an acceptable range to perform the present disclosure.

In a case where the amino acid containing reagent is in the form of a liquid, the reagent is a solution containing at least one of the amino acids listed above and may further contain components other than the amino acids listed above within an acceptable range to perform the present disclosure. A solvent is not particularly limited as long as it is suitable for dissolving the above amino acids, and those skilled in the art are able to select the solvent, as appropriate. Examples of the solvent include water and phosphate buffered saline (PBS).

In the embodiment, the additive amount of the reagent to the liquid sample is not particularly limited as long as it is an amount that the final concentration of amino acid is higher than the concentration of amino acid in the blood. Those skilled in the art are able to set the amount, as appropriate. The additive amount is preferably an amount that the final concentration of amino acid is 1 mM or more, more preferably an amount of the final concentration is 3 mM or more.

In a preferred embodiment, the recovery method of the present disclosure further comprises heat-treating a mixture obtained by mixing a liquid sample with a reagent. The temperature and time for heat-treatment of the mixture may be set in the range in which peptides in the mixture are not completely denatured by heat. The term "peptides are completely denatured" means that peptides are denatured to the extent that the peptides cannot be detected.

Those skilled in the art are able to set the heating temperature, as appropriate. The heat treatment is performed preferably at a temperature of 50° C. or higher and 260° C. or lower, more preferably a temperature of 100° C. or higher and 260° C. or lower, still more preferably a temperature of 120° C. or higher and 260° C. or lower.

Those skilled in the art are able to set the heating time, as appropriate. The heat treatment time is preferably from 30 seconds to 5 minutes, more preferably from 1 minute to 3 minutes.

The rate of temperature increase in the heat treatment is not particularly limited and those skilled in the art are able to set the rate, as appropriate.

In the embodiment, the method of heat treatment is not particularly limited as long as it is a method capable of heating the mixture at the temperatures described above. The method may be selected from known methods in the art. Examples of the method include a method of external heating by conduction and a method of heating by microwaves.

In the embodiment, the apparatus of heat-treatment is not particularly limited as long as it is an apparatus which heats the mixture at controlled temperatures. A hydrothermal reaction vessel and a microwave irradiation device are used, for example.

A precipitate considered to be a self-aggregate of protein in blood is formed from a complex of peptide and protein in blood in the mixture in the above manner. US Patent Application Publication No. 2012/0277407 has reported that almost all the molecules of the self-aggregate of albumin lose the ability to bind to peptides due to denaturation of higher order structure of albumin upon heat treatment. Consequently, the present invention is not intended to be restricted to a certain theory. A hypothesis capable of explaining the mechanism of the recovery method of the present disclosure is concerned that the peptide is liberated from the protein in blood upon the formation of the precipitate considered to be a self-aggregate of protein in blood in the recovery method of the present invention.

The precipitate is insoluble in a solvent contained in the mixture, and the precipitate is formed in the heat-treated mixture. That is, the heat-treated mixture is divided into two fractions: the precipitate considered to be a self-aggregate of protein in blood and supernatant containing peptides.

In the embodiment, the peptide liberated from protein in blood is able to be identified as the expected free form in the supernatant fraction using any known method in the art. Examples of the method include electrophoresis and mass spectrometry.

In the recovering step of the recovery method of the present disclosure, the method of removing the precipitate from the heat-treated mixture is not particularly limited. For example, the precipitate may be directly removed using a spatula. Alternatively, the precipitate may be removed using a commercially available separator or filter paper. Thus, in the recovery method of the present disclosure, peptides can be recovered by removing the precipitate from the heat-treated mixture and obtaining the supernatant fraction containing the liberated peptides.

As described above, the self-aggregate of albumin is not bound to the peptide. Therefore, it is unlikely that the precipitate considered to be a self-aggregate of the protein in blood which contains albumin as a main component binds to the peptide. However, the precipitate has water absorbability like a sponge and adsorbs a part of the supernatant containing peptides.

Therefore, the recovery method of the present disclosure may further include a step of obtaining the supernatant containing peptides from the removed precipitate. In the step of obtaining the supernatant containing peptides from the precipitate, for example, the precipitate is transferred into a tube with ultrafilter and centrifuged to squeeze the supernatant out. Alternatively, the supernatant may be obtained by stirring the precipitate with a homogenizer. The step of obtaining the supernatant containing peptides from the precipitate needs no heat treatment.

In order to remove the protein in blood, a method has been conventionally performed in which the blood sample is passed through a column adsorbing specifically albumin, albumin in the blood sample remains on the column, and a liberating form of peptides in the blood are collected. However, the report by Lowenthal et al. (Clin. Chem., vol. 51, 1933-1945 (2005)) has showed that 98% of peptides in serum are bound to albumin. That is, according to the method of the embodiment of the present invention, the peptides are also removed together with the albumin by the method of adsorbing albumin and removing peptides. Consequently, only a very small amount of the peptides are obtained.

According to the embodiment of the present invention, the peptides bound to the protein in blood such as albumin are liberated and then recovered, whereby peptides can be more efficiently recovered.

The present disclosure also includes a method of detecting a peptide. According to the detection method, the peptides liberated by the above liberating step are detected by any conventionally known method. The detection includes quantitative detection, qualitative detection, and semi-qualitative detection (determination of negativity, weak positivity or strong positivity). The results obtained by the detection method are used to obtain information such as determination of the diseases, drug susceptibility or the presence or absence of infection.

Hereinafter, the present disclosure will be described in detail with reference to embodiments; however the present disclosure is not limited thereto.

EXAMPLES

Example 1

(1) Preparation of Liquid Sample Containing Complex of Peptide and Protein in Blood ACTH partial peptide consisting of 1st to 24th amino acids of ACTH and TMR-ACTH partial peptide in which the above peptide was labeled with tetramethyl rhodamine (TMR) (a red fluorescent dye) (Biologica Co, Ltd.) were used as peptides. The ACTH is a basic peptide (isoelectric point pI=10.64). Whole blood of healthy subject (ProMed which was purchased from Dx LLC) was 10-fold diluted with 0.5× phosphate buffered saline (0.5×PBS [pH=7.4]), sodium chloride (final concentration: 68.5 mM), disodium hydrogen phosphate (final concentration: 4 mM), potassium chloride (final concentration: 1.3 mM), and potassium dihydrogen phosphate (final concentration: 0.7 mM). ACTH partial peptide was added to the resultant diluted solution at a final concentration of 2 μM to prepare a liquid sample containing a complex of peptide and protein in blood.

(2) Heat-Treatment of Liquid Sample Containing Complex of Peptide and Protein in Blood Various amino acids (L-serine, glycine, L-alanine, and L(-)-proline (manufactured by Wako Pure Chemical Industries, Ltd.), L-asparagine, L-phenylalanine, L-threonine, DL-methionine, L-tryptophan, L-valine, L-isoleucine, and L-lysine (manufactured by Sigma-Aldrich Co., LLC.), L-glutamine (manufactured by ICN Biomedicals), L-arginine (manufactured by NACALAI TESQUE, INC.), polyglycine as an amino acid derivative (manufactured by Sigma-Aldrich CO., LLC.), trimethylglycine (manufactured by Wako Pure Chemical Industries, Ltd.) or glycylglycine (manufactured by Wako Pure Chemical Industries, Ltd.) were respectively added to the liquid sample containing a complex of peptide and protein complex in blood at the final concentrations shown in Table 1 below. Thus, a mixture containing a complex of peptide and protein in blood and amino acids was obtained.

TABLE 1

| Amino acid | Concentration |
|---|---|
| Without additives | — |
| Gly (Glycine) | 2000 mM |
| Gly (Glycine) | 500 mM |
| Thr (Threonine) | 500 mM |
| Asn (Asparagine) | 150 mM |
| Gly + Thr | 500 mM + 450 mM |
| Asn + Thr | 90 mM + 300 mM |
| Ser (Serine) | 500 mM |
| Met (Methionine) | 255 mM |
| Val (Valine) | 500 mM |
| Trp (Tryptophan) | 50 mM |
| Gln (Glutamine) | 128 mM |
| Ile (Isoleucine) | 150 mM |
| Phe (Phenylalanine) | 160 mM |
| Ala (Alanine) | 500 mM |
| Pro (Proline) | 500 mM |
| TMG (Trimethylglycine) | 500 mM |
| (Gly)n (Polyglycine) | 0.05% (w/v) |
| (Gly)2 (Glycylglycine) | 500 mM |
| Lys (Lysine) | 500 mM |
| Arg (Arginine) | 500 mM |

The resultant mixture (1.5 mL) was transferred to a 10-mL volume glass test tube. The tube was sealed with a pressure resistant sealing holder for test tube of Teflon (Milestone General KK.) and placed in a microwave applicator (MultiSYNTH type, Milestone General K K.). Then, heat treatment was performed by increasing the temperature from room temperature (25° C.) to 100° C. for 30 seconds and then increasing the temperature from 100° C. to 160° C. for 1 minute. Cooling after heating was performed by blowing compressed air to the pressure resistant sealing holder from an air compressor (YC-3 R type, YAEZAKI KUATU. CO., LTD.) connected to the microwave applicator. The cooling rate was set to 20° C./min. The liquid sample (1.5 mL) not containing amino acids or an amino acid derivative was used as a control. The liquid sample was similarly sealed and subjected to the same heat-treatment. Precipitates were observed in all of the heat-treated mixtures and the heat-treated liquid sample.

(3) Detection of Peptide and Protein in Blood

The supernatant fractions of the heat-treated mixtures and the heat-treated liquid sample were used as samples and SDS-PAGE was performed on the samples.

Specifically, a sample buffer (not containing a reductant) prepared by mixing a 10× loading buffer (TAKARA BIO INC.) with a 60% (w/w) glycerol solution at a ratio of 1:1 was mixed with each of the samples. Then, electrophoresis was performed on each of the resultant mixtures at 200 V (constant voltage) for 30 minutes using NuPAGE 4-12% Bis-Tris Gel and NuPAGE MES SDS Running Buffer (both products are manufactured by Life Technologies Corporation). The used electrophoresis tank was X-Cell Sure Lock Minicell (Life Technologies Corporation) and the used electric power unit was Power Station 1000XP (ATTO Corporation). As for the gel after electrophoresis, the TMR-ACTH partial peptide was detected using a fluorescence imager (Pharos FX Molecular Imager type, Bio-Rad Laboratories, Inc.) and the HSA was detected by silver staining. In the silver staining, a silver stain kit (EZStainSilver, ATTO Corporation) was used. Respective staining steps are as follows: Immobilizing: shaking with 100 mL of a fixative (40 mL of ultrapure water, 50 mL of methanol, 10 mL of acetic acid, and a 1 mL-kit bottle S-1) for 10 minutes; Washing: shaking with 100 mL of ultrapure water three times for 10 minutes; Staining: shaking with a stain solution (100 mL of ultrapure water and a 1 mL-kit bottle S-2) for 10 minutes; Washing: shaking with 100 mL of ultrapure water for 30 seconds shaking with 100 mL of a coloring liquid (200 mL of ultrapure water, a 1 mL-kit bottle S-3, a 1 mL-kit bottle S-4) for 30 seconds; Coloring: shaking with 100 mL of a coloring liquid for 5 to 10 minutes, Terminating; shaking with 100 mL of a stop solution (100 mL of ultrapure water, 1 mL of acetic acid) for 10 minutes; Washing: shaking with 100 mL of ultrapure water twice for 5 minutes. The used shaker was In vitro shaker Wave-SI (TAITEC CORPORATION). On the basis of the results of fluorescent imaging and silver staining, the densitometry value of the peptide or protein residue was calculated using image processing software ImageJ 1.46r (NIH). The recovery rate and the purification degree were calculated according to Equations 1 and 2 below, respectively.

Recovery rate=(densitometry value when adding amino acids (after hydrothermal reaction))/(densitometry value when not adding amino acids (after hydrothermal reaction))  Equation 1

Purification degree=(gel densitometry value when not adding amino acids (after hydrothermal reaction))/(gel densitometry value when adding amino acids (after hydrothermal reaction))  Equation 2

As for the "recovery rate" in examples after the present Examples, because of a significant effect of the present invention compared to the conventional technique of performing hydrothermal reaction and recovering peptides without adding amino acids, as described in Equation 1, the ratio between the densitometry value in the case of using a measurement sample after the treatment of the present Examples (hydrothermal reaction and addition of amino acids) and the densitometry value in the case of using a measurement sample as a control (measurement sample subjected to hydrothermal treatment without adding amino acids, i.e., the conventional technique) was used. The same holds for "the purification degree". Therefore, the "recovery rate" and the "purification degree" are represented as relative values when the measurement sample as a control is defined as 1.

The band of peptide in the case of adding amino acids to be detected in fluorescence imaging is expected to be stronger than the band of peptide in the case of not adding amino acids. Accordingly, the densitometry value in the peptide band area in the case of adding amino acids is expected to be larger than the densitometry value in the band area in the case of not adding amino acids (after hydrothermal reaction). Consequently, the recovery rate calculated by Equation 1 is considered to increase when peptides can be recovered at an excellent recovery rate.

The silver-stained image of the non-amino acid-containing lane that is detected in silver staining is expected to be stronger than the silver-stained image of the amino acid-containing lane. Accordingly, the gel densitometry value of the non-amino acid-containing lane (after hydrothermal reaction) is expected to be larger than the gel densitometry value of the amino acid-containing lane. Consequently, the purification degree calculated by Equation 2 is considered to increase when peptides can be recovered at an excellent purification degree.

As an indicator for comprehensively determining the effect caused by addition of amino acids, the recovery rate×purification degree was further calculated.

The results are shown in Table 2 below.

TABLE 2

| Amino acid | Recovery rate | Purification degree | Recovery rate × Purification degree |
|---|---|---|---|
| Without additives (after hydrothermal reaction) | 1 | 1 | 1 |
| Gly 2000 mM | 2.36 | 8.12 | 19.15 |
| Gly 500 mM | 1.56 | 4.72 | 7.36 |
| Thr | 3.08 | 2.46 | 7.59 |
| Asn | 3.11 | 1.75 | 5.44 |
| Gly + Thr | 2.35 | 2.2 | 5.18 |
| Asn + Thr | 2.35 | 1.93 | 4.54 |
| Ser | 2.62 | 1.61 | 4.22 |
| Met | 1.82 | 2.11 | 3.83 |
| Val | 1.85 | 2.05 | 3.8 |
| Trp | 2.51 | 1.2 | 3.02 |
| Gln | 2.3 | 1.28 | 2.95 |
| Ile | 2 | 1.36 | 2.72 |
| Phe | 1.64 | 1.41 | 2.32 |
| Ala | 1.07 | 2.04 | 2.18 |
| Pro | 1.43 | 1.3 | 1.86 |
| TMG | 0.82 | 0.94 | 0.78 |
| (Gly)n | 0.73 | 0.98 | 0.72 |
| (Gly)2 | 0.12 | 1.03 | 0.12 |
| Lys | 0.11 | 0.68 | 0.07 |
| Arg | ND | 0.86 | ND |

As a result, in the case of adding any of glycine, threonine, asparagine, a combination of glycine and threonine, a combination of asparagine and threonine, serine, methionine, valine, tryptophan, glutamine, isoleucine, phenylalanine, alanine, and proline, the numerical value of the recovery rate×the purification degree increased, compared to the case of not adding any of the amino acids. On the other hand, even if any of trimethylglycine, polyglycine, glycylglycine, lysine, and arginine was added, an increase in the numerical value of the recovery rate×the purification degree was not observed.

This result shows that in the case of adding any of glycine, threonine, asparagine, a combination of glycine and threonine, a combination of asparagine and threonine, serine, methionine, valine, tryptophan, glutamine, isoleucine, phenylalanine, alanine, and proline, peptides can be recovered at an excellent recovery rate and purification degree, compared to the case of not adding any of the amino acids.

Example 2

(1) Preparation of Liquid Sample Containing Complex of Peptide and Protein in Blood Whole blood was 10-fold diluted with 0.5×PBS. BNP labeled with TMR (TMR-BNP) (isoelectric point pI=10.95), Iqp labeled with TMR (TMR-Iqp) (isoelectric point pI=6.75), and C-peptide labeled with TMR (TMR-C-peptide) (isoelectric point pI=3.45) (Biologica Co, Ltd.) were added to the resultant diluted solution at a final concentration of 2 μM to prepare a liquid sample containing a complex of peptide and protein in blood. Iqp is one obtained by substituting the 330th serine of 326th to 337th partial peptides of IQ and ubiquitin like domain containing protein by aspartic acid.

(2) Heat-Treatment of Liquid Sample Containing Complex of Peptide and Protein in Blood Glycine was added to the liquid sample containing the complex of peptide and protein in blood at a final concentration of 1500 mM to obtain a mixture containing a complex of peptide and protein in blood and amino acids.

The resultant mixture (1.5 mL) was transferred to a 10-mL volume glass test tube. The tube was sealed with a pressure resistant sealing holder for test tube of Teflon (Milestone General KK.) and placed in a microwave applicator (MultiSYNTH type, Milestone General K K.). Then, heat treatment was performed by increasing the temperature from room temperature (25° C.) to 100° C. for 30 seconds and then increasing the temperature from 100° C. to 160° C. for 1 minute. Cooling after heating was performed by blowing compressed air to the pressure resistant sealing holder from an air compressor (YC-3 R type, YAEZAKI KUATU. CO., LTD.) connected to the microwave applicator. The cooling rate was set to 20° C./min. As a control, the above liquid sample (1.5 mL) not containing glycine but containing various peptides was similarly sealed and subjected to the same heat-treatment. The recovery rate and purification degree obtained by using the sample was defined as 1. Precipitates were observed in all of the heat-treated mixture and liquid samples.

(3) Detection of Peptide and Protein in Blood

The supernatant fractions of the heat-treated mixtures and the heat-treated liquid sample were used as samples, and fluorescence spectra of various peptides were measured. Specifically, the above sample (0.6 mL) was placed in a quartz cell. The sample was irradiated with excitation light (540 nm) using the F-7000 type spectrophotofluorometer (manufactured by Hitachi High-Technologies Corporation), and the fluorescence spectrum at 580 nm was measured.

Based on the result, the recovery rates were calculated according to Equation 3 below. The results are shown in Tables 3 to 6 below.

Recovery rate=(fluorescent spectral peak value*when adding amino acids (after hydrothermal reaction))/(fluorescent spectral peak value when not adding amino acids (after hydrothermal reaction))  Equation 3

*: a peak value is the local maximum around 580 nm.

The fluorescent spectral peak value when adding amino acids is expected to be larger than the fluorescent spectral peak value when not adding amino acids. Therefore, the recovery rate calculated by Equation 3 is considered to increase when peptides can be recovered at an excellent recovery rate.

TABLE 3

ACTH partial peptide (isoelectric point = 10.64)

| Addition of glycine | Recovery rate | Purification degree | Recovery rate × purification degree |
| --- | --- | --- | --- |
| Not added (after hydrothermal reaction) | 1.00 | 1.00 | 1.00 |
| Added | 3.6 | 3.38 | 12.2 |

TABLE 4

BNP (isoelectric point = 10.95)

| Addition of glycine | Recovery rate | Purification degree | Recovery rate × purification degree |
| --- | --- | --- | --- |
| Not added (after hydrothermal reaction) | 1.00 | 1.00 | 1.00 |
| Added | 3.6 | 3.09 | 11.0 |

TABLE 5

Iqp (isoelectric point = 6.75)

| Addition of glycine | Recovery rate | Purification degree | Recovery rate × purification degree |
| --- | --- | --- | --- |
| Not added (after hydrothermal reaction) | 1.00 | 1.00 | 1.00 |
| Added | 3.2 | 2.50 | 8.00 |

TABLE 6

C-peptide (isoelectric point = 3.45)

| Addition of glycine | Recovery rate | Purification degree | Recovery rate × purification degree |
| --- | --- | --- | --- |
| Not added (after hydrothermal reaction) | 1.00 | 1.00 | 1.00 |
| Added | 1.8 | 2.23 | 3.95 |

As a result, peptides could be recovered at an excellent recovery rate×purification degree as follows: In the case of using TMR-ACTH (1-24), the recovered amount of peptide was 12.2 times the amount when not adding amino acids. In the case of using TMR-BNP, the recovered amount of peptide was 11.0 times the amount when not adding amino acids. In the case of using Iqp, the recovered amount of peptide was 8.00 times the amount when not adding amino acids. In the case of using C-peptide, the recovered amount of peptide was 3.95 times the amount when not adding amino acids.

The result shows that peptides having various isoelectric points can be recovered at an excellent recovery rate and purification degree by the recovery method of the present disclosure.

Example 3

The recovery rate and the purification degree were evaluated in the same manner as Example 1 except that the used amino acid was glycine at a concentration of 0 mM (no addition), 10 mM, 100 mM, 500 mM or 1500 mM, and the recovery rate was calculated similarly to Example 2. The results are shown in Table 7 below.

TABLE 7

| Final concentration of amino acid | Recovery rate | Purification degree | Recovery rate × purification degree |
|---|---|---|---|
| Without additives (after hydrothermal reaction) | 1.00 | 1.00 | 1.00 |
| 10 mM | 1.56 | 0.92 | 1.43 |
| 100 mM | 3.79 | 1.44 | 5.45 |
| 500 mM | 4.16 | 2.20 | 9.12 |
| 1500 mM | 4.89 | 5.05 | 24.6 |

As a result, peptides could be recovered at an excellent recovery rate×purification degree as follows: In the case of using glycine at a final concentration of 10 mM, the recovered amount of peptide was 1.43 times the amount when not adding amino acids. In the case of using glycine at a final concentration of 100 mM, the recovered amount of peptide was 5.45 times the amount when not adding amino acids. In the case of using glycine at a final concentration of 500 mM, the recovered amount of peptide was 9.12 times the amount when not adding amino acids. In the case of using glycine at a final concentration of 1500 mM, the recovered amount of peptide was 24.6 times the amount when not adding amino acids.

The result shows that peptides can be recovered at an excellent recovery rate and purification degree in a wide range of amino acid concentrations by the recovery method of the present invention.

Example 4

Human serum from healthy subject (purchased from ProMedD) was first 10-fold diluted with 0.5×PBS. ACTH partial peptide labeled with TMR as a model peptide was added to the diluted serum. The resultant mixture of serum and peptide (1.5 mL) was heat-treated at 160° C. Then, the fluorescence image, silver-stained image and gel densitometry data of the non-amino acid-containing sample were obtained in the same manner as Example 1. Various amino acids (glycine, asparagine, aspartic acid, glutamic acid, leucine or cysteine; the final concentrations are shown in Table 8 below) were added to the above mixture of serum and peptide to prepare amino acid-containing samples (all the samples: 1.5 mL). The samples were subjected to the same heat-treatment. Then, the fluorescence image, silver-stained image and gel densitometry data of various amino acid-containing samples were obtained in the same manner as Example 1. On the basis of the obtained data, the recovery rate and the purification degree were evaluated. The results are shown in Table 8 below.

TABLE 8

| Amino acid and final concentration | | Recovery rate | Purification degree | Recovery rate × purification degree |
|---|---|---|---|---|
| Without additives (after hydrothermal reaction) | | 1.00 | 1.00 | 1.00 |
| Glycine | 500 mM | 5.55 | 2.27 | 12.61 |
| Asparagine | 150 mM | 5.68 | 2.12 | 12.04 |
| Aspartic acid | 10 mM | 3.39 | 0.73 | 2.48 |
| | 8 mM | 14.01 | 2.27 | 31.78 |
| | 7 mM | 14.05 | 2.47 | 34.73 |
| | 5 mM | 5.78 | 1.98 | 11.44 |
| Glutamic acid | 10 mM | 13.29 | 0.83 | 11.03 |
| | 8 mM | 13.59 | 2.34 | 31.81 |
| | 7 mM | 12.39 | 2.77 | 34.36 |
| | 5 mM | 6.32 | 2.16 | 13.63 |
| Leucine | 150 mM | 5.13 | 1.33 | 6.85 |
| | 100 mM | 4.49 | 1.27 | 5.68 |
| Cysteine | 500 mM | 15.39 | 0.90 | 13.83 |
| | 100 mM | 11.92 | 1.24 | 14.72 |
| | 50 mM | 8.30 | 1.67 | 13.87 |
| | 20 mM | 3.94 | 1.59 | 6.24 |

As a result, in the case of adding any of glycine, asparagine, aspartic acid, glutamic acid, leucine, and cysteine, the numerical value of the recovery rate×the purification degree increased, compared to the case of not adding any of the amino acids.

The result shows that peptides can be recovered at an excellent recovery rate and purification degree even if any of glycine, asparagine, aspartic acid, glutamic acid, leucine, and cysteine is added as compared to the case of not adding amino acids.

Example 5

The fluorescence image, silver-stained image and gel densitometry data were obtained in the same manner as Example 4 except that, as an amino acid, asparagine was used at a final concentration of 150 mM, and the heating temperature was 130° C., 140° C., 150° C. or 160° C. As for the process of increasing the temperature to 130° C., 140° C. or 150° C., the temperature was increased from room temperature (25° C.) to 100° C. for 30 seconds. Thereafter, the temperature was increased at a rate of 1° C./sec. The temperature was increased from 100° C. to each temperature, and then the temperature was maintained at each temperature for 30 seconds, 20 seconds, and 10 seconds, respectively. The results are shown in Table 9 below.

TABLE 9

| Experimental conditions | Recovery rate | Purification degree | Recovery rate × purification degree |
|---|---|---|---|
| Without addition of amino acid, heating temperature: 160° C. | 1.00 | 1.00 | 1.00 |
| Addition of Asn, heating temperature: 160° C. | 6.84 | 2.46 | 16.83 |
| Addition of Asn, heating temperature: 150° C. | 4.70 | 2.01 | 9.46 |
| Addition of Asn, heating temperature: 140° C. | 3.89 | 2.12 | 8.22 |
| Addition of Asn, heating temperature: 130° C. | 2.44 | 2.13 | 5.21 |

As a result, in the case of increasing the temperature to the range of 130° C. to 160° C. in the heat-treating step after addition of Asn, the recovery rate increased about 2 times to about 7 times that in the case of not adding amino acids, the purification degree increased about 2 times to about 2.5 times that in the case of not adding amino acids, and the recovery rate×purification degree of peptide increased about 5 times to about 17 times that in the case of not adding amino acids.

The result shows that peptides can be recovered at an excellent recovery rate and purification degree in a wide range of heating temperatures by the method of recovering a peptide of the present invention.

Example 6

Figure 1B:
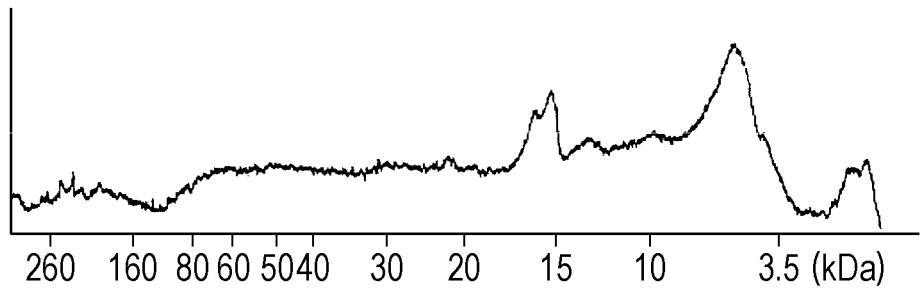
FIG. 1B is a graph showing the band intensity of SDS-PAGE gel.

As the peptide to be recovered, hen egg-white lysozyme hydrochloride having 129 residues (Wako 120-02674 Lot LAQ6504; about 15 kDa) was used. The lysozyme was dissolved in PBS. A 2 M glycine solution was added to the resultant mixture to prepare a measurement sample 1. The concentration of lysozyme in the measurement sample 1 was 10 mg/mL, and the concentration of glycine was 1 M. A solution (without hydrothermal treatment) prepared by mixing the measurement sample 1, a tris phosphoric acid buffer (Tris•HCl [pH=7.0] (final concentration: 100 mM)), sodium phosphate (final concentration: 0.4 mM), and NaCl (final concentration: 6 mM) in an equivalent amount was used, and SDS-PAGE was performed on the solution. A graph of the band intensity of the gel is shown in FIG. 1A. The measurement sample 1 (1.4 mL) was transferred to a 10-mL volume vial, and the hydrothermal reaction was performed on the sample in the same manner as Example 1. A solution prepared by mixing the measurement sample 1 after the hydrothermal reaction, the tris phosphoric acid buffer, sodium phosphate, and NaCl in an equivalent amount was used, and SDS-PAGE was performed on the solution. A graph of the band intensity of the gel is shown in FIG. 1B.

In FIG. 1A, a large peak was observed at a position of 15 kDa. This corresponds to the size of the lysozyme dissolved in the sample. In FIG. 1B, a peak can be confirmed at a position of 15 kDa. However, the peak decreased greatly, compared to the peak of the PBS solution of lysozyme (FIG. 1A). In contrast, peaks were detected at a position of 3.5 to 10 kDa and a position of less than 3.5 kDa. This suggests that the lysozyme was fragmented. Therefore, the results of FIG. 1B show that when the method of recovering a peptide of the present disclosure is used, the lysozyme itself can be recovered and the fragment of the lysozyme can also be recovered.

Comparative Example 1

An attempt to recover peptides was made in the same manner as Example 4 except that a basic amino acid arginine (5 mM, 2 mM or 0.5 mM) or lysine (5 mM, 2 mM or 0.5 mM) was used as an amino acid.

However, the protein in blood did not aggregate when these amino acids were used, and peptides could not be recovered.

What is claimed is:

1. A method of recovering a peptide, comprising:
liberating a peptide from albumin by mixing a liquid sample containing a complex of the peptide and albumin with a reagent containing a free neutral amino acid, a free acidic amino acid, or both; and
recovering the liberated peptide,
wherein the liquid sample is blood, plasma or serum,
wherein the liberating step comprises a step of heat-treating the mixture of the liquid sample and the reagent, wherein said heat-treating is performed under conditions where the peptide in the liquid sample is not completely denatured by heat, wherein in said heat-treating, the mixture is heated to a temperature within the range of 120° C.-260° C.,
wherein said method further comprises removing a precipitate comprising albumin which is formed after the heat-treating step and before the recovering step,
wherein the concentration of the amino acid in the mixture of the liquid sample and the reagent is 1 mM or more,
wherein the free neutral amino acid is selected from the group consisting of glycine, threonine, asparagine, serine, methionine, valine, tryptophan, glutamine, isoleucine, phenylalanine, alanine, proline, leucine, and cysteine, and wherein the free acidic amino acid is selected from the group consisting of aspartic acid and glutamic acid.

2. The method according to claim 1, wherein the heat-treating is performed by irradiation with microwaves.

3. The method according to claim 1, wherein the mixture is heated for a period of from 30 seconds to 5 minutes in the heat-treating.

4. A method of detecting a peptide, comprising:
liberating a peptide from albumin by mixing a liquid sample containing a complex of the peptide and albumin with a reagent containing a free neutral amino acid, a free acidic amino acid, or both; and
detecting the liberated peptide,
wherein the liquid sample is blood, plasma or serum,
wherein the liberating step comprises a step of heat-treating the mixture of the liquid sample and the reagent, wherein said heat-treating is performed under conditions where the peptide in the liquid sample is not completely denatured by heat, wherein in said heat-treating, the mixture is heated to a temperature within the range of 120° C.-260° C.,
wherein said method further comprises removing a precipitate comprising albumin which is formed after the heat-treating step and before the detecting step,
wherein the concentration of the amino acid in the mixture of the liquid sample and the reagent is 1 mM or more,
wherein the free neutral amino acid is selected from the group consisting of glycine, threonine, asparagine, serine, methionine, valine, tryptophan, glutamine, isoleucine, phenylalanine, alanine, proline, leucine, and cysteine, and wherein the free acidic amino acid is selected from the group consisting of aspartic acid and glutamic acid.

5. The method according to claim 4, wherein
the liquid sample is heated for a period of from 30 seconds to 5 minutes in the heat-treating.

6. A method of recovering a peptide, comprising:
mixing a liquid sample and a reagent, the reagent comprising a free neutral amino acid, a free acidic amino acid, or both, whereby the peptide is liberated from albumin; and
recovering the liberated peptide
wherein the liquid sample is blood, plasma or serum,
wherein the liberating step comprises a step of heat-treating the mixture of the liquid sample and the reagent, wherein said heat-treating is performed under conditions where the peptide in the liquid sample is not completely denatured by heat, wherein in said heat-treating, the mixture is heated to a temperature within the range of 120° C.-260° C., wherein said method further comprises removing a precipitate comprising albumin which is formed after the heat-treating step and before the recovering step, wherein the concentration of the amino acid in the mixture of the liquid sample and the reagent is 1 mM or more, wherein the free neutral amino acid is selected from the group consisting of glycine, threonine, asparagine, serine, methionine, valine, tryptophan, glutamine, isoleucine, phenylalanine, alanine, proline, leucine, and cysteine, and wherein the free acidic amino acid is selected from the group consisting of aspartic acid and glutamic acid.

* * * * *